United States Patent
Okediji

(10) Patent No.: US 6,824,569 B2
(45) Date of Patent: Nov. 30, 2004

(54) RECIPROCAL GAIT ORTHOTIC AND PROSTHETIC DEVICE

(76) Inventor: Adeola Okediji, 312 Baldwin Rd., Hempstead, NY (US) 11550

( * ) Notice: Subject to any disclaimer, the term of this patent is extended or adjusted under 35 U.S.C. 154(b) by 0 days.

(21) Appl. No.: 10/269,371

(22) Filed: Oct. 11, 2002

(65) Prior Publication Data

US 2004/0073149 A1 Apr. 15, 2004

(51) Int. Cl.⁷ .................................................. B61F 2/60
(52) U.S. Cl. ........................................ 623/30; 602/62
(58) Field of Search ............................. 623/27, 30, 31; 602/62, 63, 5, 16

(56) References Cited

U.S. PATENT DOCUMENTS

| | | | | |
|---|---|---|---|---|
| 2,573,866 A | * | 11/1951 | Murphy | 128/80 |
| 3,995,324 A | * | 12/1976 | Burch | 3/1.2 |
| 4,697,808 A | * | 10/1987 | Larson et al. | 272/70 |
| 6,039,707 A | * | 3/2000 | Crawford et al. | 602/5 |

* cited by examiner

*Primary Examiner*—Bruce E Snow
(74) *Attorney, Agent, or Firm*—Cohen, Pontani, Lieberman & Pavane

(57) ABSTRACT

A reciprocal gait apparatus for use as an orthotic or prosthetic is disclosed. In one embodiment, the apparatus comprises a torso vest securable about the torso of a patient, a leg support securable on a leg of a patient and a hip joint coupled to and disposed between the torso vest and leg support, and two resilient members respectively disposed substantially anterior and posterior about the hip joint and coupled to the torso vest and leg support. A first resilient member flexes the leg support in a forward direction in response to lifting of said leg support. A second resilient member moves the leg support in a backward direction once the leg support has been substantially flexed in the forward direction along a range of motion for said leg support. Another embodiment of the reciprocal gait apparatus comprise a gear assembly and two belts for implementing reciprocal gait.

20 Claims, 3 Drawing Sheets

RECIPROCAL GAIT ORTHOTIC AND PROSTHETIC DEVICE

BACKGROUND OF THE INVENTION

1. Field of the Invention

The present invention is a device for people with a physical disability, injury or disease. More specifically, the present invention is directed to a reciprocal gait orthosis device for assisting handicapped people to stand, walk or ambulate.

2. Description of the Related Art

People with physical disabilities of their lower extremities have traditionally used a manual or machine operated wheelchair to provide mobility. However, there are several problems associated with the use of the wheelchair. For example, the wheelchair can only move within buildings and vehicles which are specifically wheelchair-accessible. Moreover, the person is confined to a seat of the wheelchair and is prone to develop leg tightness and pressure sores. If the wheelchair user is a child, the inability to move around with other children may also cause the user to develop low self esteem and become depressed.

In response to these problems associated with the conventional use of wheelchairs, orthotic devices have been developed to assist people to stand, walk and ambulate and thus become more mobile. One common type of orthotic device is a hip-knee-ankle-foot orthosis (HKAFO) device having a trunk section, two leg sections and two lateral hip joints to connect the two legs sections to the trunk section. Locks are typically provided with each of the hip joints and are placed in a unlocked position when the person wearing the HKAFO device intends to sit down.

The locks are placed in a locked position when the person uses a walker or forearm crutch with the HKAFO device for standing and moving with a swing-through or hopping type gait. Although the use of a HKAFO device provides greater mobility of areas not previously accessible with the use of a wheelchair, the person using the HKAFO device must move both legs together along a single plane. The HKAFO device is also heavy and cumbersome. Thus, the person using the HKAFO device must expend much of their energy to move both legs together in a swing-through or swivel gait pattern. Moreover, for those individuals with some strength in their lower extremities, the need to lock the hip joint for using the HKAFO device inhibits the gradual rehabilitation of these extremities.

The reciprocating gait orthosis (RGO) device is a type of orthotic device designed to overcome the aforementioned problems associated with HKAFO devices. A typical RGO device comprises a dual-cable system connected to leg supports so as to alternatively transfer energy in the movement of one leg to the other leg. With the dual-cable system, one cable causes flexion of one leg while the other cable causes extension of the other leg in a reciprocal gait manner. One exemplary RGO device is disclosed in U.S. Pat. No. 4,946,156 to Hart.

However, the dual-cable system is heavy and cumbersome to use. RGO devices having this dual-cable system are also more expensive than HKAFO devices. Moreover, the dual-cable system is not configured for enabling ambulation of people having hip joint contracture or tightness or significant knee flexion contracture, for example, of more than 15 degrees of joint contracture. Thus, people having such contractures would have to ambulate with the hip and knee joints locked with a swing-through or swivel-gait pattern as with the HKAFO device. The required energy for such swing-through or swivel gait ambulation is significant and limits the rehabilitation of individuals having some strength in their hip and lower leg and decreased mobility in other ranges.

Therefore, people having significant hip or knee contractures must first use a HKAFO device while undergoing intensive stretching, joint mobilization and possibly surgery to reduce such contractures. Once the contracture is decreased, the person is now fitted with a RGO device and continues rehabilitation using the RGO device. However, gradual rehabilitation using HKAFO and RGO devices often cannot reduce hip and knee contractures. In this case, the user cannot use a conventional RGO device to perform reciprocal ambulation. There is thus a need in the art for a novel RGO device that is lightweight and is suitable for people having various degrees of contractures at the hip and knee joint.

SUMMARY OF THE INVENTION

The present invention is directed to a reciprocal gait apparatus for use as an orthotic or prosthetic. In one embodiment, the apparatus comprises a torso vest securable about the torso of a patient, a leg support securable on a leg of a patient and a hip joint coupled to and disposed between the torso vest and leg support, and two resilient members respectively disposed substantially anterior and posterior about the hip joint and coupled to the torso vest and leg support. A first resilient member flexes the leg support in a forward direction in response to lifting of said leg support. A second resilient member moves the leg support in a backward direction once the leg support has been substantially flexed in the forward direction along a range of motion for said leg support. Another embodiment of the reciprocal gait apparatus comprise a gear assembly and two belts for implementing reciprocal gait.

BRIEF DESCRIPTION OF THE DRAWINGS

In the drawings.

In the drawings, wherein like reference characters delineate similar elements.

DETAILED DESCRIPTION OF THE PRESENTLY PREFERRED EMBODIMENTS

Figure 1:
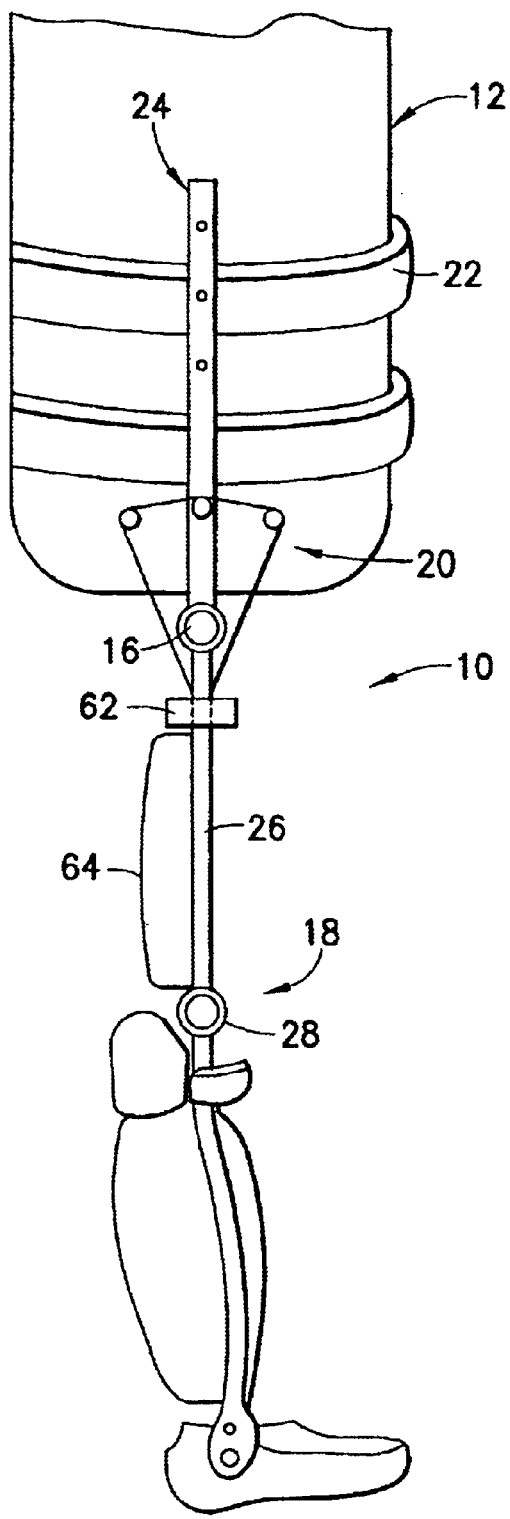
FIG. 1 is right-side elevation view of the reciprocal gait orthosis (RGO) device of the present invention.

Referring to FIG. 1, a reciprocal gait orthosis (RGO) device 10 is shown. In one embodiment, the RGO device 10 comprises a torso vest 12, hip joint 16, leg support 18, and reciprocal gait assembly 20. Although FIG. 1 depicts the RGO device 10 for the right leg, the present invention likewise applies to the left leg.

Torso vest 12 is a rigid padded structure that is made and custom fitted for the patient or person using RGO device 10 in a conventional manner. Torso vest 12 is securely fitted around the corresponding torso of a patient using one or more torso straps 22. Each torso strap 22 is typically made from VELCRO, nylon or other material suitable for straps.

Hip joint 16 is disposed laterally along the hip of the user and enables rotation thereof. Hip joint 16 is connected to torso vest 12 with a torso connector 24 and to a leg support 18 with a leg connector 26. The angle of hip joint 16 between torso connector 24 and leg connector 26 is adjustable to an angle of the natural hip position for a particular user of RGO device.

Leg support 18 is preferably fitted along each leg of the user for providing support thereof. Leg support 18 includes a knee joint 28 for providing flexibility between the thigh and shin or lower leg. Knee joint 28 can be either locked or unlocked depending on the use of the RGO device 10. For example, knee joint 28 is generally locked if the user's knee is weak and still needs rehabilitation. However, knee joint 28 is generally unlocked if RGO device 10 is used for assisting walking or ambulation. The angle of knee joint 16 is also adjustable to an angle of the natural knee position for a particular user of RGO device 10.

In accordance with the present invention, reciprocal gait assembly 20 comprises a mechanism for providing reciprocal gait to the user of RGO device 10 so as to assist the user to stand, walk or ambulate. Reciprocal gait assembly 20 assists the backward extension of one leg while assisting the forward flexion of the other leg. Although gait assembly 20 is often used bilaterally for both legs of the user or patient, it may also be used unilaterally for one leg. This latter situation occurs if the user or patient needs to rehabilitate only one side of the lower body.

Figure 2:
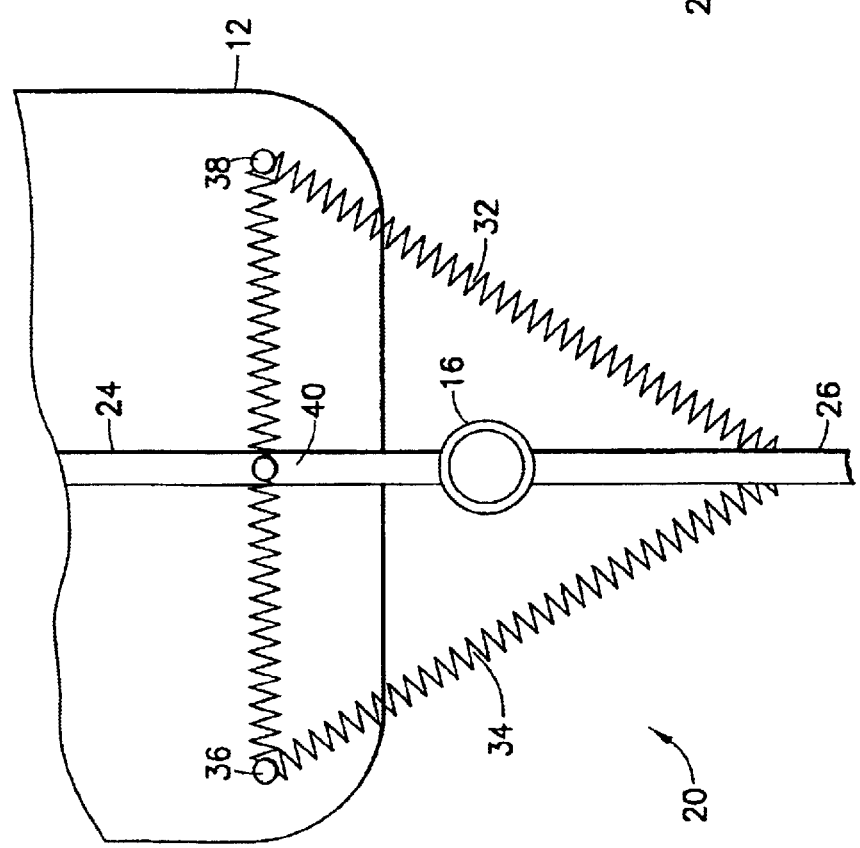
FIG. 2 is a detailed view of a first embodiment of a reciprocal gait assembly in the RGO device of FIG. 1.

FIG. 2 shows a first embodiment of reciprocal gait assembly 20 comprising one resilient member 32 disposed substantially anterior to hip joint 16 and another resilient member 34 disposed substantially posterior to hip joint 16. One end of each resilient member 32, 34 is secured to the torso vest 12 (either at torso connector 24 or on vest 12 itself) and the other end of resilient member is secured to the leg member 18 at leg connector 26. Examples of resilient members 32, 34 include a spring, an elastic band, and the like.

Bolts or other types of support members 36, 38, 40 are illustratively secured on torso vest 12 and/or the torso connector 24 for supporting the extension and contraction of resilient members 32, 34. The position of support bolts 36, 38 on torso vest 12 is adjustable in accordance to the angle at hip joint 16 or the range of motion of the leg for which reciprocal gait assembly 20 is fitted.

In one configuration of assembly 20, resilient member 32 contracts to flex leg connector 26 and the user's leg forward relative to torso vest 12 and torso connector 24 while the other leg extends backward. The other resilient member 34 contracts to extend leg connector 26 and the user's leg backward relative to torso vest 12 and torso connector 24 while the other leg flexes forward. This extension and flexion of alternative legs is the reciprocal gait motion generated in accordance with the present invention.

Although the movement of legs were in response to contraction of resilient members 32, 34, this movement can also occur in response to corresponding extensions of resilient members 32, 34. For example, resilient member 32 can expand to extend the leg in a backward motion and resilient member 34 can expand to flex the leg in a forward motion. Additionally, the resistance of resilient members 32, 34 may be tailored with respect to various factors including but not limited to the weight of the user, user's speed of ambulation, and the user's range of ambulation.

Figure 3:
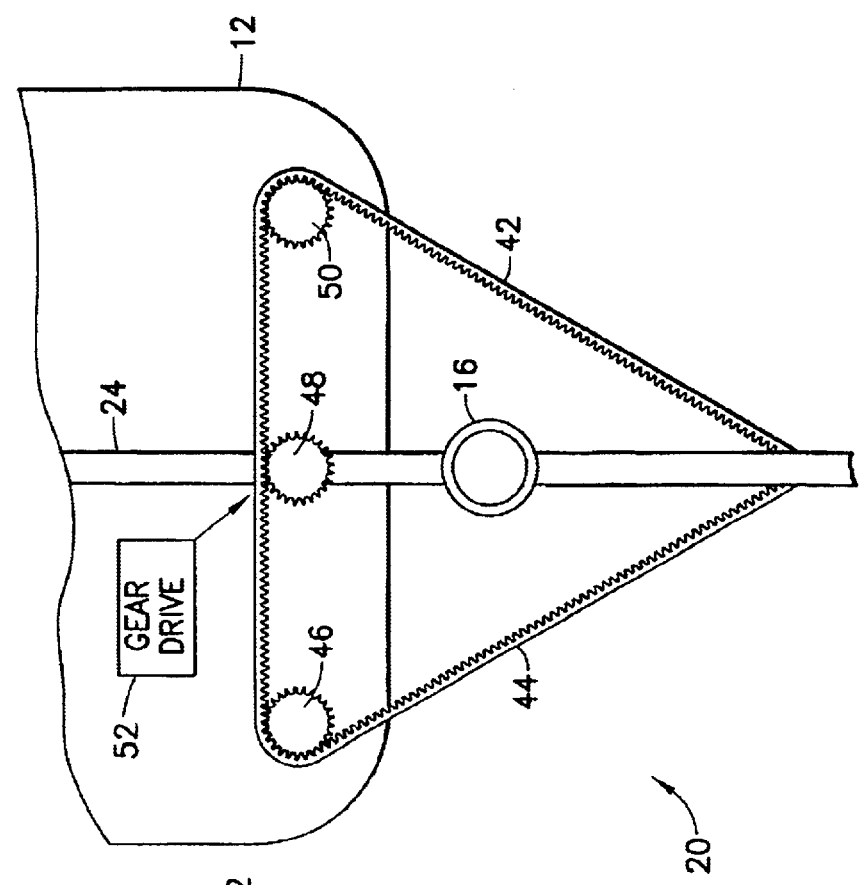
FIG. 3 is a detailed view of a second embodiment of a reciprocal gait assembly in the RGO device of FIG. 1.

FIG. 3 shows a second embodiment of reciprocal gait assembly 20 comprising two belts 42, 44, gears 46, 48, 50 and a drive mechanism 52. One belt 42 is disposed substantially anterior to hip joint 16 while the other belt 44 is disposed substantially posterior to hip joint 16. Gears 46, 48, 50 are secured to torso vest 12 and/or torso connector 24 for driving the belts 42, 44 to flex and extend the leg secured to the assembly 20. Although shown as separate elements, gears 46, 48, 50 may alternatively be interconnected. Gear mechanism 48 comprises components for driving one or more of the gears 46, 48, 50. For example, gear mechanism 48 may comprise a processor for providing an electrical signal and a motor for driving at least one gear 46, 48 or 50 in response to the electrical signal.

The reciprocal gait assembly 20 of FIG. 4 is configured to pull belt 42 backwards in the posterior direction so as to flex the leg forward while the other leg extends backwards. Assembly 20 also pulls belt 44 forwards in the anterior direction so as to extend the leg backward while the other leg is flexed forward. Belts 42, 44 are shown as separate but may be configured as one belt that can be driven with one or more gears.

Referring back to FIG. 1, the RGO device 10 may also include additional features to improve its use thereof. For example, RGO device 10 may also include an optional locking mechanism 62 proximate to or located at the hip joint 16. If hip joint 16 is locked, the RGO device 10 can be used as a HKAFO device. RGO device may also include a thigh support 64 along leg connector 26 and between hip joint and leg member 18. Thigh support 64 provides additional support for the user around the thigh and is typically custom-made for the user. Thigh support 64 may include but is not limited to carbon graphite laminate of smooth thermoplastic.

The locking of either hip joint 16 or knee joint 28 for each leg is performed in accordance to the needs or the progress of the patient or user. During the initial stage of rehabilitation and training in the use of RGO device 10, the user may need to lock both hip joint 16 and knee joint 28. In this case, RGO device 10 operates like a conventional HKAFO device that restricts the user to ambulate with a swing-through or swivel gait pattern. The patient will also need to use another device such as a walker or bilateral crutches for ambulation.

Once the patient or user gains strength and/or becomes better coordinated in using RGO device 10, hip joint 16 can be unlocked while knee joint 28 remains locked. This mode of use is most suitable for patients or users having some hip flexor strength and with or without 15–20 degrees hip or knee contracture or tightness. However, patients or user without strength in their hip flexors and with at least 20–30 degrees of hip and knee contracture can also use the RGO device 10 of the present invention.

Figure 4C:
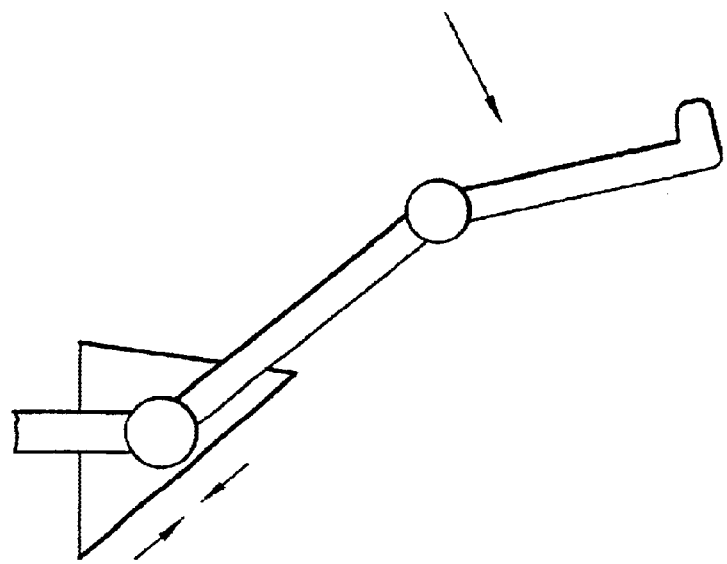
FIGS. 4A to 4C illustrate the operation of the RGO device with the reciprocal gait assembly of FIG. 2.
Figure 4B:
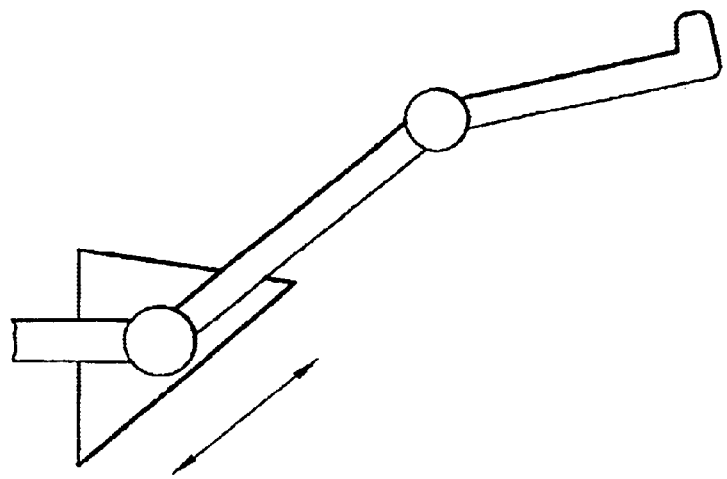
Figure 4A:
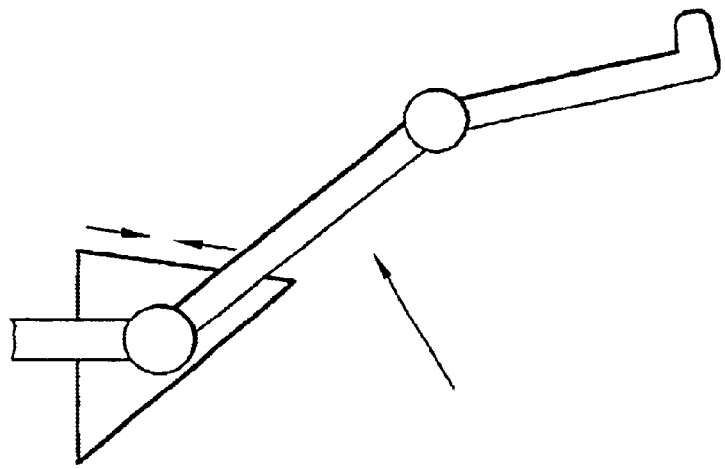

The operation of the RGO device 10 is best illustrated with respect to FIGS. 4A to 4C. To implement reciprocal gait using device 10, it is preferable but not necessary that hip joint 16 is unlocked, knee joint 28 is locked, and resilient members 32, 34 are taut (stretched) and adjusted to the user's hip angle. Although operation of RGO device 10 is described with the reciprocal gait assembly 20 of FIG. 2, RGO device 10 would operate in a similar manner if the assembly of FIG. 3 is used.

Suppose the user or patient with approximately ten percent knee contracture is initially in a upright position and then leans back at the one side of the torso, for example the left side. This transfers the weight of the user onto the leaned upon (left) leg and release the weight from the right or opposite leg. The anterior resilient member 32 of weight-released (right) leg then contracts and causes the leg to flex forward as shown in FIG. 4A.

The inertia of the forward moving leg causes the user to take a step forward and shifts weight onto the flexed (right) leg as shown in FIG. 4B. The posterior resilient member 34 expands or stretches as the user takes the step with the right leg. Once the range of motion of the (right) leg is reached, the posterior resilient member 34 contracts and causes the (right) leg to extend backwards as shown in FIG. 4C.

While the user shifts weight onto the flexed (right) leg, the anterior resilient member 32 of the other (left) leg contracts and causes the other (left) leg to flex outward as the initially moved (right) leg extends backwards. Such extension of one leg while flexing the other leg represents the reciprocal gait performed in accordance with the present invention.

Although the reciprocating gait assembly 20 preferably uses both resilient members 32, 34, there are instances where it is desired to use only one resilient member 32 or 34. For example, if a user or patient has increased strength in their hip extensors and decrease strength in their hip flexors, then only the use of resilient member 32 is required. However, if the user or patient has increased strength in their hip flexors and decreased strength in their hip extensors, then only the use of resilient member 34 is required for facilitating hip flexion. Therefore, other embodiments of reciprocal gait assembly 20 or RGO device 10 having assembly 20 may include one resilient member 32 or 34 or one belt 42 or 44.

The knee joint 28 also can be locked depending on the strength of a user's or patient's knee extensors. For example, if the patient has increased strength in their knee extensors, the knee joint can be unlocked for rehabilitation purposes. If the knee extensor is stronger for one leg, then the knee joint 28 of that leg can be unlocked while the knee joint 28 for the other leg is locked.

Thus the RGO device 10 of the present invention is capable of providing reciprocal ambulation for people with decreased strength in their legs regardless of the amount of hip or knee contracture. This allows people with at least 10 to 20 degrees of knee contracture to reciprocally ambulate using the RGO device 10 of the present invention. The RGO device 10 can be used either unilaterally for one leg or bilaterally for both legs. Although preferably used for orthotics, the device of the present invention can also be used as a prosthetic device.

Accordingly, while there has been shown and described and pointed out various features of the invention as applied to preferred embodiments thereof, it will be understood that various omissions and substitutions and changes in the form and details of the methods described and devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A reciprocal gait apparatus comprising:
    a torso vest securable about the torso of a patient;
    a leg support securable on a leg of a patient;
    a hip joint coupled to and disposed between said torso vest and said leg support;
    a first resilient member disposed substantially anterior about said hip joint and coupled to said torso vest and said leg support for flexing said leg support in a forward direction in response to lifting of said leg support; and
    a second resilient member disposed substantially posterior about said hip joint and coupled to said torso vest and said leg support for moving said leg support in a backward direction once said leg support has been substantially flexed in the forward direction along a range of motion for said leg support.

2. The reciprocal gait apparatus according to claim 1, wherein said first resilient member and said second resilient member comprise a spring.

3. The reciprocal gait apparatus according to claim 1, wherein said first resilient member and said second resilient member comprise an elastic band.

4. The reciprocal gait apparatus according to claim 1, wherein said first resilient member contracts to move said leg support forward and said second resilient member contracts to move said leg assembly backward.

5. The reciprocal gait apparatus according to claim 1, wherein said first resilient member expands to move said leg support backward and said second resilient member expands to move said leg support forward.

6. The reciprocal gait apparatus according to claim 1, further comprising a support member secured on said torso vest for guiding movement of said first resilient member and second resilient member.

7. The reciprocal gait apparatus according to claim 6, wherein said support member comprises a bolt.

8. The reciprocal gait apparatus according to claim 1, wherein a position of said support member on said torso vest is adjustable in accordance with an angle between the torso and the leg of the patient at said hip joint.

9. A reciprocal gait apparatus comprising:
    a torso vest securable about the torso of a patient;
    a leg support securable on a leg of a patient;
    a hip joint coupled to and disposed between said torso vest and said leg support;
    a first belt disposed substantially anterior about said hip joint and coupled to said torso vest and said leg support for flexing said leg support in a forward direction when said first belt is pulled in a backward direction;
    a second belt disposed about said hip joint and coupled to said torso vest and said leg support for moving said leg support in a backward direction when said second belt is pulled in a forward direction; and
    a gear assembly secured about said torso vest and coupled to said first belt and said second belt for pulling said first belt and said second belt.

10. The reciprocal gait apparatus of claim 9, wherein said gear assembly comprises a motor and at least one gear coupled to said motor and said first and second belts, wherein said motor drives said at least one gear and said at least one gear drives said first and second belts.

11. The reciprocal gait apparatus of claim 10, wherein the position of said at least one gear on the torso vest is adjustable in accordance with an angle between the torso and the leg of the patient at said hip joint.

12. The reciprocal gait apparatus of claim 10, wherein at least one of the power and speed of said motor is adjustable in accordance with an angle between the torso and the leg of the patient at said hip joint.

13. An assembly for providing reciprocal gait for an orthotic device comprising a torso vest securable about the torso of a patient, a leg support securable on a leg of a patient, and a hip joint coupled to and disposed between the torso vest and the leg support, said assembly comprising:

a first resilient member disposed substantially anterior about the hip joint and coupled to the torso vest and the leg support for flexing the leg support in a forward direction in response to lifting of the leg support; and a second resilient member disposed substantially posterior about the hip joint and coupled to said torso vest and the leg support for moving said leg support in a backward direction once the leg support has been substantially flexed in the forward direction along a range of motion for the leg support.

14. The assembly according to claim 13, further comprising a support member securable on the torso vest for guiding movement of said first resilient member and second resilient member.

15. The assembly according to claim 14, wherein said support member comprises a bolt.

16. A reciprocal gait apparatus comprising:

a torso vest securable about the torso of a patient;

a leg support securable on a leg of a patient;

a hip joint coupled to and disposed between said torso vest and said leg support; and a resilient member disposed about said hip joint and coupled to said torso vest and said leg support, said resilient member being configurable for one of flexing said leg support in a forward direction and extending said leg support in a backward direction, said leg support flexing in the forward direction in response to lifting of said leg support and extending in the backward direction once said leg support has been substantially flexed in the forward direction along a range of motion for said leg support.

17. The reciprocal gait apparatus of claim 16, further comprising a support member securable on the torso vest proximate to said hip joint for guiding movement of said resilient member.

18. The reciprocal gait apparatus according to claim 16, wherein a position of said support member on the torso vest is adjustable in accordance with an angle between the torso and the leg of the patient at the hip joint.

19. A reciprocal gait apparatus comprising:

a torso vest securable about the torso of a patient;

a leg support securable on a leg of a patient;

a hip joint coupled to and disposed between said torso vest and said leg support;

a first resilient member disposed substantially anterior about said hip joint and coupled to said torso vest and said leg support for flexing said leg support in a forward direction in response to lifting of said leg support; and a second resilient member disposed substantially posterior about said hip joint and coupled to said torso vest and said leg support for moving said leg support in a backward direction once said leg support has been substantially flexed in the forward direction along a range of motion for said leg support;

wherein said first resilient member and said second resilient member comprise an elastic band.

20. A reciprocal gait apparatus comprising:

a torso vest securable about the torso of a patient;

a leg support securable on a leg of a patient;

a hip joint coupled to and disposed between said torso vest and said leg support;

a first resilient member disposed substantially anterior about said hip joint and coupled to said torso vest and said leg support for flexing said leg support in a forward direction in response to lifting of said leg support; and a second resilient member disposed substantially posterior about said hip joint and coupled to said torso vest and said leg support for moving said leg support in a backward direction once said leg support has been substantially flexed in the forward direction along a range of motion for said leg support;

wherein said support member comprises a bolt.

* * * * *